(12) United States Patent
Yokoe et al.

(10) Patent No.: US 8,426,451 B2
(45) Date of Patent: Apr. 23, 2013

(54) ORAL SOLID PREPARATION AND METHOD OF MANUFACTURING THE SAME

(75) Inventors: Junichi Yokoe, Osaka (JP); Keisuke Nakajo, Osaka (JP); Naohisa Katayama, Osaka (JP); Toshiya Kai, Osaka (JP)

(73) Assignee: NIPRO Corporation, Osaka (JP)

( * ) Notice: Subject to any disclaimer, the term of this patent is extended or adjusted under 35 U.S.C. 154(b) by 824 days.

(21) Appl. No.: 12/149,039

(22) Filed: Apr. 25, 2008

(65) Prior Publication Data

US 2008/0269301 A1    Oct. 30, 2008

(30) Foreign Application Priority Data

Apr. 27, 2007    (JP) .................................. 2007-118797

(51) Int. Cl.
*A61K 31/44*    (2006.01)
*A61K 31/4422*    (2006.01)

(52) U.S. Cl.
USPC ........... 514/356; 424/10.3; 424/490; 424/493

(58) Field of Classification Search ................... 514/356
See application file for complete search history.

(56) References Cited

FOREIGN PATENT DOCUMENTS

| | | |
|---|---|---|
| EP | 1 813 274 A1 | 8/2007 |
| EP | 1 839 650 A1 | 10/2007 |
| JP | 55-022645 A | 2/1980 |
| JP | 2000-191516 A | 7/2000 |
| JP | 2003-104887 | 4/2003 |
| JP | 2003-104888 A | 4/2003 |
| JP | 2006-306754 A | 11/2006 |
| WO | 98/04243 | 2/1998 |
| WO | 2006/038661 A1 | 4/2006 |
| WO | 2006/070845 | 7/2006 |
| WO | 2007/005292 A1 | 5/2007 |

*Primary Examiner* — Frederick Krass
*Assistant Examiner* — Adam C Milligan
(74) *Attorney, Agent, or Firm* — Kubovcik & Kubovcik

(57) ABSTRACT

An oral solid preparation including a base compound and a powdery or granular additive colored with a colorant and a method of manufacturing an oral solid preparation including the steps of: coloring an additive with a colorant, mixing the resultant additive with a base compound, and tableting the mixture.

1 Claim, 1 Drawing Sheet

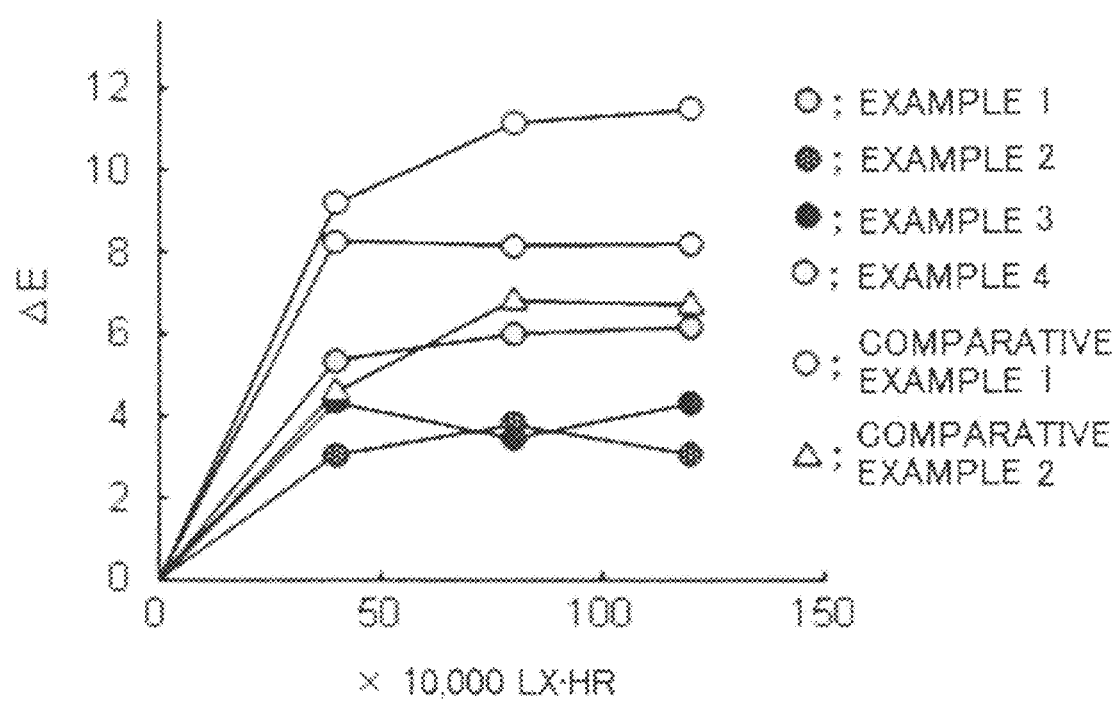

ORAL SOLID PREPARATION AND METHOD OF MANUFACTURING THE SAME

BACKGROUND OF THE INVENTION

1. Field of the Invention

The present invention relates to an oral solid preparation and a method of manufacturing the same, and more specifically to an oral solid preparation that is stable to light and a method of manufacturing the same.

2. Description of the Related Art

Some of base compounds having drug effects are extremely unstable to light. For example, amlodipine, which is a dihydropyridine calcium antagonist, has a long half-life in blood and is widely used in the clinical field as an antihypertensive drug for once-a-day ingestion.

However, in general, dihydropyridine drugs have problems of light stability. Among the drugs, amlodipine is a compound that is relatively hard to decompose by light, but in the case where amount of the exposed light is much, the compound is decomposed, resulting in lowering of its medicinal properties.

Accordingly, formulation of amlodipine requires a technique for ensuring light stability.

For example, there is suggested a tablet having light stability improved by coating a tablet of a dihydropyridine derivative with a film agent containing ferric oxide (for example, JP 2003-104888 A).

However, in the case of a preparation that is required to degrade within 30 seconds in the oral cavity like an oral disintegrating tablet, only such a technique to coat the whole tablet may impair rapid degradability, resulting in insufficient exertion of its functions. It is technically possible to produce particles by coating the whole of a drug, but the coating may impair the ability of the drug to be rapidly eluted from the particle and prevent sufficient exertion of the drug effects after an administration of the drug.

Moreover, there is suggested a method of enhancing the light stability of an uncoated dihydropyridine drug. Examples of the method include a method that includes adding yellow ferric oxide to nifedipine to suppress the production amount of an oxidant produced by light and to prevent a reduction in the base component content (JP 55-22645 A).

However, this document has no description about amlodipine.

On the other hand, another document introduces the fact that blending of ferric oxide can prevent discoloration or decomposition of amlodipine and a pharmaceutically acceptable salt by light (JP 2006-306754 A).

However, this document describes only prevention of discoloration or decomposition caused by yellow ferric oxide and does not describe a sufficient study on the effects of other colorants.

BRIEF SUMMARY OF THE INVENTION

The present invention has been made in view of the above-mentioned problems, and an object of the present invention is to provide an oral solid preparation improved in light stability by preventing discoloration or decomposition of a light-unstable drug by light, and a method of manufacturing the same.

The inventors of the present invention have made extensive studies to achieve the above-mentioned object, and as a result, they have surprisingly found out that blend of a dye in an amount smaller than usual can suppress photodecomposition of a light-unstable drug and prevent discoloration of the surface of a tablet, thereby completing the present invention.

An oral solid preparation of the present invention is characterized by including a base compound and a powdery or granular additive colored with a colorant.

A method of manufacturing an oral solid preparation of the present invention is characterized by including the steps of coloring an additive with a colorant, mixing the resultant additive with a base compound, and tableting the mixture.

According to the present invention, it is possible to effectively prevent discoloration or decomposition of a light-unstable drug by light and even in the case of using a small amount of a colorant, to produce an oral solid preparation improved in light stability.

BRIEF DESCRIPTION OF THE DRAWINGS

FIG. 1 is a graph showing changes in color tones in Examples 1 to 4 and Comparative Examples 1 and 2.

DETAILED DESCRIPTION OF THE INVENTION

The oral solid preparation of the present invention includes a base compound and an additive.

The base compound is not particularly limited, and it may be one or two or more of, for example, the following: medicines for airsickness, antipyretic analgesics, aromatic stomachics, stomachics and digestives, antacids, vitamin preparations, analeptics, enzyme preparations, analeptic health medicines, anti-inflammatory drugs, antirheumatic drugs, arthrifuges, antihistaminics, antiallergic agents, antibiotic preparations, synthetic antimicrobials, agents for dental and oral use, bronchodilators, antitussive agents, expectorants, sleeping sedatives, antianxiety drugs, antiepileptic drugs, psychoneurotic agent, autonomic agents, agents affecting the central nervous system, spasmolytics, cerebral metabolism improving agents, cerebral circulation improving agents, antiparkinson agents, Alzheimer's drugs, cardiotonics, antiarrhythmic drugs, diuretics, vasoconstrictors, vasodilators, antihypotensive agents, agents for hyperlipidemia, antidiarrheals, peptic ulcer agents, cathartics, hormone preparations, and diabetic drugs, and prodrugs. Among them, a base compound that is a light-unstable drug is effective.

For example, the base compound may be one or two ore more of the following compounds: dihydropyridine derivatives such as amlodipine and nifedipine; antiviral/HIV protease inhibitors such as ritonavir and saquinavir; antihyperlipemic drugs such as clofibrate; iodos such as sodium iopodate and sodium iodide; highly-unsaturated fatty acid derivatives such as ethyl icosapentate (EPA) and docosahexaenoic acid (DHA); carcinoids such as lycopene, bixin, β-carotene, xanthophylls, and rutin; vitamin derivatives such as ubidecarenone (metabolic cardiotonic drug), ubiquinone such as coenzyme $Q_{10}$ (coenzyme Q), and mecobalamin; indomethacin; pranoprofen; warfarin potassium; colchicines; diazepam; syrosingopine; norethisterone; piretanide; propericyazine; perphenazine; mequitazine; medazepam; menatetrenone; indenolol hydrochloride; reserpine; sofalcone; bromocriptine mesylate; bufetolol hydrochloride; oxprenolol hydrochloride; and azulenes; and pharmaceutically acceptable salts thereof. Among them, the dihydropyridine derivatives, in particular, amlodipine or a pharmaceutically acceptable salt thereof is effective.

The form of the base compound is not particularly limited, and examples thereof include powder, solid, and granule. The size of the base compound is not particularly limited, and for example, in the case where the base compound is ingested as an oral disintegrating tablet, the size can be appropriately adjusted in consideration for the feeling on the tongue or the like. Specifically, the base compound may have a mean particle size of about 5 μm to about 50 μm. The base compound may be formed into an appropriate shape and size by, for example, a method of uniformizing particle sizes using a sieve, a membrane filter, etc., or a method of pulverizing the base compound using a ball mill pulverizer, a hammer mill pulverizer, a pin mill pulverizer, etc. Meanwhile, the base compound may be a granulated product obtained by a method known in the art.

The additive contained in the oral solid preparation of the present invention is not particularly limited, and it may be any one generally used in the medical field. For example, excipients, disintegrators, lubricants, binders, solubilizers, fluidization agent, sweeteners, flavors, foaming agents, surfactants, and antiseptic agents may be used singly or in combination of two or more.

Among those additives, one or two or more additives or components having the largest weight or relatively large weights are colored with a colorant. In the present invention, the "coloring with a colorant" does not include mixing of an additive and a colorant but includes nearly uniform adhesion of a colorant to at least the surface of an additive or includes permeate of a colorant to at least the surface layer of an additive.

In general, the coloring with a colorant can be achieved by using a suspension or a solution (preferably solution) containing the colorant. That is, the coloring can be carried out by: dissolving or suspending a colorant in a liquid that is generally used in the art, such as an organic solvent such as water or ethanol; and applying the resultant solution or suspension to an additive by a method known per se. The application of the colorant solution to an additive can be performed based on the pan coating method, flow coating method, roller coating method, etc. using an apparatus such as a sloping pan, a ventilation-type rotary cylindrical coating apparatus, a general-purpose flow coating apparatus, a Wurster coating apparatus, a complex roller flow coating apparatus, etc. by a spray, a pump, a spray gun, a liquid delivery line, etc.

Meanwhile, another coloring method includes a method including the steps of: pulverizing dye particles; and adhering the dye and coloring one or two or more additives or components having the largest weight or relatively large weights to be coated using an apparatus such as a dry coating apparatus (mechanofusion, manufactured by Hosokawa Micron Corporation).

The blending amount of a colorant may be adjusted depending on the species of a base compound used, the species of the colorant, etc. For example, the amount is suitably about 0.01 to 5% by weight, preferably about 0.01 to 4% by weight, more preferably 0.02 to 4% by weight, 0.1 to 3% by weight based on the weight of the base compound. From another point of view, the amount is preferably about 0.0001 to 2% by weight, about 0.0002 to 1.5% by weight, about 0.001 to 2% by weight, about 0.001 to 1.5% by weight, about 0.005 to 1.5% by weight based on the total of an oral solid preparation.

In the case where a colorant solution which have the concentration about 0.05 w/v % to 5 w/v % is applied to an additive, the volume of the solution is suitably about 400 to 1,000 mL, more suitably about 100 to 400 mL based on 1 kg of the additive.

As described above, if a colorant solution is applied to an additive, the colorant solution is permeated into the spaces between the additive particles, to the surfaces of the particles, optionally to the interiors of the particles, thereby achieving almost uniform adhesion or permeation of the colorant to at least the surface layers of the additive. This can achieve uniform diffusion of a colorant to an additive without unevenness, thereby imparting sufficient light stability to a base compound even in the case of using a smaller amount of the colorant.

The additive may be in the form of powder or granule. That is, the additive may have a mean particle size of about 5 to 500 μm, about 5 to 300 μm, or about 5 to 200 μm. The additive having such a form may be produced by a method of pulverizing a base compound using various pulverizers or the like, by uniformizing the particle sizes using various members or the like, or by granulation using a method known in the art.

The granulation may be performed by wet granulation or dry granulation. In the case of the wet granulation, granulation can be performed by using various apparatus such as a fluidized-bed granulation drier, a stirring granulator, a cylindrical extrusion granulator, and a roller fluidized-bed granulation coating machine or by spray drying method. In the case of the dry granulation, granulation can be performed by using various apparatus such as a dry granulator including a roller compactor and a slug tableting machine. In particular, the additive is preferably formed by the wet granulation method. This is because the wet granulation method can produce particles having uniform particle sizes and reduce the ratio of fine powder compared with the dry granulation method, resulting in production of granules with excellent formability, in general.

In the case of granulation of an additive, other additives as described below may be optionally added.

The colorant to be used in the present invention is not particularly limited, and examples thereof include yellow ferric oxide, ferric oxide (red), orange essence, brown ferric oxide, caramel, light anhydrous silicic acid, food blue No. 5, food yellow No. 4, food yellow No. 4 aluminum lake, food yellow No. 5, food red No. 2, food red No. 3, food red No. 102, food blue No. 2, talc, fluorescein sodium, green tea powder, vitamin C, food lake dyes, carotenoid dyes, flavonoid dyes, and quinone dyes. Among them, water-soluble colorants are preferable from the viewpoint of easiness of production process. In addition, the colorant is preferably a tar dye, particularly preferably yellow No. 5. This is because yellow No. 5 is water-soluble, so yellow No. 5 can be used easily in preparation of a liquid colorant, and the ADI (acceptable daily intake; an amount of a substance that can be daily ingested by humans over a lifetime without an appreciable health risk) of yellow No. 5 is 0 to 2.5 mg/kg, which is estimated to be safer than, for example, ferric oxide (0 to 0.5 mg/kg).

Examples of the excipient include glucose, fructose, lactose, saccharose, reduced maltose, and sugar alcohols (such as D-mannitol, erythritol, sorbitol, xylitol, trehalose, maltitol, and lactitol). Those may be used singly or in combination of two or more.

Examples of the disintegrator include crosspovidone, carboxy starch sodium, carboxymethyl starch sodium, starch, partially pregelatinized starch, corn starch, lactose, calcium carbonate, precipitated calcium carbonate, calcium citrate, light anhydrous silicic acid, synthetic aluminum silicate crystalline cellulose, hydroxypropyl cellulose with a low substitution degree, croscarmellose, croscarmellose sodium, carboxymethylcellulose calcium, carmellose, and hydroxypropyl starch. Those may be used singly or in combination of two or more. Among them, croscarmellose, carboxy starch sodium, carmellose, starch, hydroxypropyl starch, and crosspovidone are suitably used. The amount of the disintegrator is generally about 0.1% by weight or more, more preferably about 0.5% by weight or more, particularly preferably 2% by weight or more based on the total of an oral disintegrating tablet. In addition, the amount is about 30% by weight or less, more preferably about 25% by weight or less, particularly preferably 15% by weight or less.

Examples of the lubricant include magnesium stearate, calcium stearate, talc, sucrose fatty acid ester, polyethylene glycol, stearic acid, light anhydrous silicic acid, hydrogenated rapeseed oil, hydrogenated castor oil, glycerine fatty acid ester, sodium stearyl fumarate, sodium benzoate, L-leucine, and L-valine. Those may be used singly or in combination of two or more.

The binder may be, for example, a water-soluble substance. Examples thereof include gelatin, agar, alginic acid, sodium alginate, dextrin, xanthan gum, gum Arabic powder, hydroxyethylcellulose, hydroxypropylcellulose, hydroxypropylmethylcellulose, polyvinylpyrrolidone, partially saponified polyvinyl alcohol, methylcellulose, pullulan, partially pregelatinized starch, and saccharides. Those may be used singly or in combination of two or more.

Examples of the solubilizer include magnesium oxide, calcium oxide, sodium citrate, magnesium chloride, sodium carbonate, and sodium hydrogen carbonate. Those may be used singly or in combination of two or more.

Examples of the fluidization agent include hydrous silicon dioxide and light anhydrous silicic acid.

Examples of the sweetener include aspartame, saccharin sodium, dipotassium glycyrrhizinate, stevia, and thaumatin. Those may be used singly or in combination of two or more.

Examples of the flavor include mint, lemon, and orange.

Examples of the foaming agent include a tartrate, a citrate, and a bicarbonate.

Examples of the surfactant include: anionic surfactants such as sodium alkyl sulfate; non-ionic surfactants such as sucrose fatty acid ester, polyoxyethylene sorbitan fatty acid ester, polyoxyethylene fatty acid ester, and polyoxyethylene castor oil derivative. Those may be used singly or in combination of two or more.

Examples of the antiseptic agent include benzoic acid, parahydroxybenzoic acid, and salts thereof.

The oral solid preparation of the present invention may be formulated into various forms of preparations. The forms may be, for example, tablets, oral disintegrating tablets, capsules, pills, troches, granules, and powders; and other forms for oral administration, such as suspensions, emulsions, liquids, and syrups. Among them, the preparation is effective when it is in the form of a tablet, in particular, an oral disintegrating tablet.

The shape of the tablet, in particular, the oral disintegrating tablet is not particularly limited, and it may be a disk, doughnut, polygonal, plate, spherical, elliptical, or caplet shape. Among them, the tablet preferably has a disk shape, which is a general tablet shape. The size of the tablet is not particularly limited, and it is suitably a slightly large size to avoid direct swallowing. For example, the tablet is preferably about 3 to 30 mm in diameter and about 1 to 10 mm in thickness. The oral solid preparation of the present invention particularly preferably has no coating layer in the outermost surface, i.e., it is preferably an uncoated tablet. If the tablet is in such a form, the feeling on the tongue, degradability, etc. of the oral disintegrating tablet can be particularly suitably maintained.

The oral solid preparation of the present invention, in particular, the oral disintegrating tablet can be manufactured by mixing a base compound with a powdery or granular additive colored with a colorant as described above and molding the mixture.

The mixing can be performed by optionally adding the above-mentioned additive or the like according to a method known in the art using a known apparatus or the like. The mixing is preferably performed without moistening or humidification to avoid changing or impairing the coloring state formed with a colorant. The moistening or humidification means addition of water in an amount larger than about 5% of the total weight of the oral disintegrating tablet.

The molding of the mixture is suitably performed by compacting the mixture using a known apparatus or the like according to a method known in the art. The apparatus for compression molding may include, for example, a tableting mortar and upper and lower tableting pestles, and it may be a hydraulic hand press machine, a single-punch tableting machine, or a rotary tableting machine.

The compression molding is preferably performed while adjusting the conditions so that the resultant tablet has an appropriate hardness, for example, about 30 N or more, more preferably about 40 N or more and has an appropriate independent space to rapidly be disintegrated as an oral disintegrating tablet. For example, the tableting pressure is not particularly limited and may be appropriately adjusted depending on used apparatus, principles, tablet size, species of a base compound, etc. In the case of using the above-mentioned apparatus, for example, the tableting pressure is suitably about 50 kg/cm$^2$ or more and about 1,500 kg/cm$^2$ or less, generally about 300 kg/cm$^2$ or more and about 1,000 kg/cm$^2$ or less. The compression molding is suitably performed under non-moistening or non-humidification conditions.

In the case where the oral solid preparation of the present invention is formed by compression molding, even if at least the surface layer of an additive is almost uniformly colored, the colorant is not always present in a final solid preparation. For example, the particle shapes of the additive are sometimes deformed by compression molding so that the particle spaces of the additive and/or base compound are filled. This may cause elimination or the like of the colorant from the surface layers of the additive, but the colorant is considered to be uniformly or periodically distributed in the oral solid preparation. As described above, at least the surface layers of an additive are almost uniformly colored, and if the additive is mixed with the base compound, the additive that is generally blended in an amount larger than the base compound may enclose the particles of the base compound. This achieves adhesion of the colorant to the base compound or arrangement of the colorant around the base compound, and a smaller amount of the colorant can improve light stability of the base compound.

Hereinafter, the solid oral preparation and method of manufacturing the same of the present invention will be described in detail.

EXAMPLES 1 TO 4 AND COMPARATIVE EXAMPLE 1 AND 2

Food yellow No. 5 was weighed according to Table 1 and dissolved in 50 g of purified water, to thereby prepare coating solutions 1 to 4.

TABLE 1

|  | Food yellow No. 5 |
| --- | --- |
| Coating solution 1 | 62.6 mg |
| Coating solution 2 | 313 mg |
| Coating solution 3 | 1,252 mg |
| Coating solution 4 | 12.5 mg |

Subsequently, 500 g of D-mannitol (mean particle size: about 40 μm) was added to a Wurster fluidized-bed granulator (MP-SPC-01, manufactured by Powrex Corporation) and coated under the conditions of 70° C. intake air temperature, 0.80 m³/sec intake air flow, 15.0 to 22.5 NL/min atomized air volume, and 4.0 to 6.0 g/min coating solution 1 spray rate, to thereby prepare colored D-mannitol 1 (mean particle size: about 60 μm).

In the same way as above, the coating solutions 2 to 4 were separately sprayed to D-mannitol, to thereby prepare colored D-mannitols 2 to 4.

Thereafter, the components described in Table 2 and 3 were weighed and mixed, followed by tableting using a rotary tableting machine to produce tablets each having a weight of 200 mg (a hardness of 50 N), to thereby prepare oral disintegrating tablets that disintegrate within 20 seconds in the oral cavity.

TABLE 2

| Composition | Example 1 | Example 2 | Example 3 | Example 4 |
|---|---|---|---|---|
| Amlodipine besilate | 10.4 | 10.4 | 10.4 | 10.4 |
| Mannitol for direct tableting (Parteck 100M) | 79.8 | 79.8 | 79.8 | 79.8 |
| Crystalline cellulose | 45.0 | 45.0 | 45.0 | 45.0 |
| Crosspovidone | 30.0 | 30.0 | 30.0 | 30.0 |
| Aspartame | 6.0 | 6.0 | 6.0 | 6.0 |
| Sucrose fatty acid ester | 6.0 | 6.0 | 6.0 | 6.0 |
| Magnesium stearate | 3.0 | 3.0 | 3.0 | 3.0 |
| D-mannitol | | | | |
| Colored D-mannitol 1 | 119.8 | | | |
| Colored D-mannitol 2 | | 119.8 | | |
| Colored D-mannitol 3 | | | 119.8 | |
| Colored D-mannitol 4 | | | | 119.8 |
| Yellow ferric oxide | | | | |

TABLE 3

| Composition | Comparative Example 1 | Comparative Example 2 |
|---|---|---|
| Amlodipine besilate | 10.4 | 10.4 |
| Mannitol for direct tableting (Parteck 100M) | 79.8 | 79.5 |
| Crystalline cellulose | 45.0 | 45.0 |
| Crosspovidone | 30.0 | 30.0 |
| Aspartame | 6.0 | 6.0 |
| Sucrose fatty acid ester | 6.0 | 6.0 |
| Magnesium stearate | 3.0 | 3.0 |
| D-mannitol | 119.8 | 119.8 |
| Colored D-mannitol 1 | | |
| Colored D-mannitol 2 | | |
| Colored D-mannitol 3 | | |
| Colored D-mannitol 4 | | |
| Yellow ferric oxide | | 3.0 |

In the cases of Comparative Examples 1, yellow ferric oxide powder was not added in oral disintegrating tablets. In the cases of Comparative Examples 2, yellow ferric oxide powder was optionally blended without dissolving it in a liquid, followed by tableting, to thereby prepare oral disintegrating tablets.

Table 4 shows the blending ratio of the colorant (% by weight) based on the base compound in Example 1-4 and Comparative Example 2.

TABLE 4

| Example 1 | Example 2 | Example 3 | Example 4 | Comparative Example 2 |
|---|---|---|---|---|
| 0.14 | 0.72 | 2.88 | 0.03 | 28.85 |

Table 5 shows the blending ratio of the colorant (% by weight) based on the total of the oral solid preparation in Example 1-4 and Comparative Example 2

TABLE 5

| Example 1 | Example 2 | Example 3 | Example 4 | Comparative Example 2 |
|---|---|---|---|---|
| 0.005 | 0.025 | 0.100 | 0.001 | 0.990 |

TEST EXAMPLE

A light stability test was performed for the oral disintegrating tablets prepared in Examples 1 to 4 and Comparative Examples 1 and 2. FIG. 1 shows changes in color tone under fluorescent lights of 400,000, 800,000, and 1,200,000 lx·hr, and Table 4 shows oxidant production amounts.

In this test, the changes in color tone were measured using a color difference meter (Z-300A, manufactured by Nippon Denshoku Industries Co., Ltd.).

Meanwhile, the amounts of an oxidant (2-[(2-aminoethoxy)methyl]-4-(o-chlorophenyl)-6-methyl-3,5-pyridinecarboxylate 3-ethylester 5-methylester) were determined through an analysis by liquid chromatography.

HPLC Analysis Method

Column: Octadecyl group-bonded silica gel (mean particle size 3 μm, inner diameter 4.6×length 150 mm) (manufactured by Kanto Kagaku, product name: Mightysil RP-18 GP 150-4.6 (3 μm))

Column temperature: a constant temperature of about 35° C.

Mobile phase A: water/trifluoroacetic acid (5,000:1)

Mobile phase B: acetonitrile/trifluoroacetic acid (5,000:1)

Liquid delivery of mobile phase: the mix ratio of mobile phases A and B is changed as shown in Table 6 to control the concentration gradient.

TABLE 6

| Time after injection (min) | Mobile phase A | Mobile phase B |
|---|---|---|
| 0 to 30 | 80 to 20 | 20 to 80 |
| 30 to 45 | 20 | 80 |

TABLE 7

| | Oxidant amount (%) | | |
|---|---|---|---|
| | 0 lx · hr | 400,000 lx · hr | 800,000 lx · hr |
| Example 1 | 0.016 | 0.227 | 0.356 |
| Example 2 | 0.031 | 0.221 | 0.352 |
| Example 3 | 0.012 | 0.155 | 0.295 |
| Example 4 | 0.014 | 0.218 | 0.488 |
| Comparative Example 1 | 0.035 | 0.287 | 0.530 |
| Comparative Example 2 | 0.026 | 0.272 | 0.399 |

As shown in FIG. 1, in the case of Comparative Example 1, the color tone was significantly changed, and the rates of change in the color tone (ΔE values) exceeded 10 with increases in lx values.

On the other hand, in the cases of Examples 1 to 3, changes in the color tones were suppressed. Especially, in the cases of Examples 2 and 3, the ΔE values were lower than that in the case of Comparative Example 1 (4 or lower). Meanwhile, in the case of Example 4, the color tone was approximately constant regardless of increases in lx values, and the ΔE values were about 8.

Moreover, as shown in Table 7, in the case of Comparative Example 1 where uncolored D-mannitol was used, the amounts of the produced oxidant were high, while in the cases of the preparations of Examples 1 to 4, the amounts of the produced oxidant were reduced depending on the coloring degrees of D-mannitol.

Those results revealed that, in the cases of the preparation containing D-mannitol coated with yellow No. 5, both of the changes in color tones and the amounts of the produced oxidant were suppressed.

This application claims priority of Japanese patent application No. 2007-118797 filed Apr. 27, 2007, which is incorporated herein by reference.

What is claimed is:

1. A method of manufacturing an oral solid preparation comprising the steps of:
    coloring an excipient with food yellow No. 5;
    mixing the resultant excipient with amlodipine or a pharmaceutically acceptable salt thereof; and
    tableting the mixture in the form of an oral disintegrating tablet;
    wherein the step of coloring the excipient with food yellow No. 5 is performed by suspending or dissolving the food yellow No. 5 in a liquid and spraying the resultant liquid colorant to the excipient.

* * * * *